(12) United States Patent
Bertrand et al.

(10) Patent No.: US 6,281,154 B1
(45) Date of Patent: Aug. 28, 2001

(54) COMPOUNDS HAVING ONE GROUP 13 ELEMENT, BOUND WITH ONE MONO- OR DI-ANIONIC TRIDENT LIGAND, A METHOD OF PREPARATION AND APPLICATION THEREOF AS POLYMERIZATION CATALYSTS

(75) Inventors: Guy Bertrand, Pechbusque; Jean Bernard Cazaux, Aramon, both of (FR); Norbert Emig, Monthey (CH); Régis Reau, La Chapelle des Fougeretz (FR)

(73) Assignees: Societe de Conseils de Recherches et d'Applications Scientifiques (S.C.R.A.S); Centre National de la Recherche Scientifique (CNRS), both of (FR)

( * ) Notice: Subject to any disclaimer, the term of this patent is extended or adjusted under 35 U.S.C. 154(b) by 0 days.

(21) Appl. No.: 09/171,940

(22) PCT Filed: Apr. 30, 1997

(86) PCT No.: PCT/FR97/00773

§ 371 Date: Oct. 28, 1998

§ 102(e) Date: Oct. 28, 1998

(87) PCT Pub. No.: WO97/42197

PCT Pub. Date: Nov. 13, 1997

(30) Foreign Application Priority Data

May 2, 1996 (EP) .................................. 96400938

(51) Int. Cl.$^7$ .............................. B01J 31/18; C07F 5/00; C08F 4/52; C08G 65/10; C08G 65/12
(52) U.S. Cl. .................. 502/150; 502/152; 502/167; 502/200; 502/202; 546/2; 546/6; 546/10; 546/13; 549/206; 549/210; 549/213; 556/172; 556/173; 556/174; 556/175; 526/204; 526/217; 526/266; 526/270; 526/273; 528/92; 528/94; 528/354; 528/359; 528/416; 528/417; 528/421
(58) Field of Search .................................. 502/150, 152, 502/167, 200, 202; 546/2, 6, 10, 13; 549/206, 210, 213; 556/172, 173, 174, 175, 182, 187; 526/178, 180, 183, 185, 177, 204, 217, 266, 270, 273; 528/92, 94, 354, 359, 416, 417, 421

(56) References Cited

PUBLICATIONS

Copy of Chem. Abstracts, vol. 59 (1 page), No. 3, Mehrotra et al.

Primary Examiner—Robert Dawson
Assistant Examiner—Jeffrey B. Robertson
(74) Attorney, Agent, or Firm—Bierman, Muserlian and Lucas (57) ABSTRACT

Novel compounds having one group 13 element bound with one mono- or di-anionic tridentate ligand, a method of preparation thereof and use thereof as a copolymerization catalyst.

15 Claims, 6 Drawing Sheets

COMPOUNDS HAVING ONE GROUP 13 ELEMENT, BOUND WITH ONE MONO- OR DI-ANIONIC TRIDENT LIGAND, A METHOD OF PREPARATION AND APPLICATION THEREOF AS POLYMERIZATION CATALYSTS

This application is a 371 of PCT/FR97/00773 filed Apr. 30, 1997.

Certain mono- and di-anionic tridentate ligands are known as ligands for transition metals.

Thus, the $(Ph_2PCH_2SiMe_2)_2N^-$ derivative was used to prepare iridium complexes (Fryzuk et al., Angew. Chem. Ed. Engl. (1990), 29, 73) and the $[(Me_3SiNCH_2CH_2)_2NSiMe_3]^{2-}$ derivative was used to prepare zirconium dichloride complexes (Cloke et al., J. Chem. Soc., Dalton Trans. (1995), 25). Boron derivatives having the $[(O_2CCH_2)_2NCH_3]^{2-}$ ligand are also known (Contrepas et al., J. Organomet. Chem. (1986), 307,1). Moreover, aluminium derivatives having the $[NH(CH_2CH_2O)_2]^{2-}$ ligand have also been described (Mehrotra et al., J. Indian Chem. Soc. (1962), 39, 677–82).

The use of Lewis acids having an element of group 13 in organic synthesis is also known (Yamamoto, H. in Organometallics in Synthesis; Schlosser, M., Ed.; John Wiley and Sons Ltd.: West Sussex, England, 1994, Chapter 7) as well as catalysts for the polymerization of heterocycles (Inoue, Acc. Chem. Res. (1996) 29,39). Inoue et al. demonstrated that the catalysts having ligands of porphyrine type were capable of producing polymers having a polymolecularity index close to one (J. Chem. Soc., Chem. Commun. (1985), 1148; Chem. Lett. (1987), 991; Makromol. Chem. (1981) 182, 1073). Moreover, these catalysts can be used to prepared alternating or block copolymers (Inoue et al., J. Am. Chem. Soc. (1983) 105, 1304; J. Am. Chem. Soc. (1985) 107, 1358; Macromolecules (1984) 17, 2217). These two properties are due to the fact that a living polymer is generated.

However, these catalytic systems use porphyrine ligands which are expensive and difficult to access, resulting in an increased cost. Furthermore, in order to increase the activity, it is necessary to add Lewis acids, which increases the complexity of the catalytic systems (Inoue et al., Macromolecules (1994) 27, 2013; Macromolecules (1995) 28, 651).

The problem was therefore to find catalytic systems which were more efficient, easier to synthesize and more economical than those previously recommended.

The present invention relates to new compounds having an element of group 13 linked to a mono- or di-anionic tridentate ligand, a process for their preparation and their use in particular as polymerization catalysts.

A subject of the invention is thus the products of general formula 1 and 2

(1)

(2)

in which
M represents an element of group 13;
$R_M$ represents the hydrogen atom, a halogen atom or one of the following radicals, substituted (by one or more identical or different substituents) or non-substituted: alkyl, cycloalkyl, aryl, alkoxy, cycloalkoxy, aryloxy, alkylthio, cycloalkylthio or arylthio, in which said substituent is a halogen atom, the alkyl, nitro or cyano radical;
A and B represent, independently, a carbonated chain with 2 to 4 carbon atoms, optionally substituted by one of the following substituted (by one or more identical or different substituents) or non-substituted radicals: alkyl, cycloalkyl or aryl, in which said substituent is a halogen atom, the alkyl, nitro or cyano radical;
$L_1$, $L_2$ and $L_3$ represent, independently, a group of formula $-E_{15}(R_{15})-$ in which
$E_{15}$ is an element of group 15 and
$R_{15}$ represents the hydrogen atom; one of the following substituted (by one or more identical or different substituents) or non-substituted radicals: alkyl, cycloalkyl or aryl, in which said substituent is a halogen atom, the alkyl, nitro or cyano radical; a radical of formula $RR'R''E_{14}-$ in which $E_{14}$ is an element of group 14 and R, R' and R'' represent, independently, the hydrogen atom or one of the following substituted (by one or more identical or different substituents) or non-substituted radicals: alkyl, cycloalkyl, aryl, alkoxy, cycloalkoxy, aryloxy, alkylthio, cycloalkylthio or arylthio, in which said substituent is a halogen atom, the alkyl, nitro or cyano radical; or a radical of formula $SO_2R'_{15}$ in which $R'_{15}$ represents a halogen atom, an alkyl, haloalkyl or aryl radical optionally substituted by one or more substituents chosen from the alkyl, haloalkyl radicals and halogen;
$X_1^-$ represents a non-coordinating anion with respect to element M;
$R_1$ represents a hydrogen atom, a radical of formula $RR'R''E_{14}-$ in which $E_{14}$, R, R' and R'' have the same definitions as above, or one of the following radicals, substituted (by one or more identical or different substituents) or non-substituted: alkyl, cycloalkyl or aryl, in which said substituent is a halogen atom, the alkyl, nitro or cyano radical.

In the definitions indicated above, the expression halogen represents a fluorine, chlorine, bromine or iodine atom, preferably chlorine. The expression alkyl preferably represents a linear or branched alkyl radical having from 1 to 6 carbon atoms and in particular an alkyl radical having from 1 to 4 carbon atoms such as the methyl, ethyl, propyl, isopropyl, butyl, isobutyl, sec-butyl and tert-butyl radicals.

The term haloalkyl preferably designates the radicals in which the alkyl radical is as defined above and is substituted by one or more halogen atoms as defined above such as, for example, bromoethyl, trifluoromethyl, trifluoroethyl or also pentafluoroethyl. The alkoxy radicals may correspond to the radicals in which the alkyl radical is as defined above. The methoxy, ethoxy, isopropyloxy or tert-butyloxy radicals are preferred. The alkylthio radicals preferably represent the radicals in which the alkyl radical is as defined above such as, for example, methylthio or ethylthio.

The cycloalkyl radicals are chosen from the saturated or unsaturated monocyclic cycloalkyls. The saturated monocyclic cycloalkyl radicals can be chosen from the radicals having from 3 to 7 carbon atoms such as the cyclopropyl, cyclobutyl, cyclopentyl, cyclohexyl or cycloheptyl radicals. The unsaturated cycloalkyl radicals can be chosen from the cyclobutene, cyclopentene, cyclohexene, cyclopentanediene, cyclohexadiene radicals. The cycloalkoxy radicals can correspond to radicals in which the cycloalkyl radical is as defined above. The cyclopropyloxy, cyclopentyloxy or cyclohexyloxy radicals are preferred. The cycloalkylthio radicals can correspond to radicals in which the cycloalkyl radical is as defined above such as for example cyclohexylthio.

The aryl radicals can be of mono- or polycyclic type. The monocyclic aryl radicals can be chosen from the phenyl radicals optionally substituted by one or more alkyl radicals, such as tolyl, xylyl, mesityl, cumenyl. The polycyclic aryl radicals can be chosen from the naphthyl, anthryl, phenanthryl radicals. The aryloxy radicals can correspond to radicals in which the aryl radical is as defined above. The phenoxy, 2,4,6-tritertiobutylphenoxy, tolyloxy or mesityloxy radicals are preferred. The arylthio radicals preferably designate the radicals in which the aryl radical is as defined above such as for example in phenylthio.

The $X_1^-$ anion can be chosen from non-coordinating anions with respect to element M such as the tetrafluoroborate, tetraphenylborate, tetrachloroaluminate, hexafluorophosphate, hexafluoroantimonate, trifluoromethanesulphonate or perchlorate anions.

A more particular subject of the invention is the products of general formula 1 and 2 as defined above, characterized in that M represents a boron, aluminium or gallium atom;

$R_M$ represents the hydrogen atom, a halogen atom and in particular chlorine, or the methyl radical;

A and B represent, independently, a carbonated chain with 2 to 4 carbon atoms, and in particular a carbonated chain with 2 carbon atoms;

$L_1$ and $L_2$ represent, independently, a radical of formula —$E_{15}(R_{15})$— in which $E_{15}$ is a nitrogen or phosphorus atom and $R_{15}$ represents a radical of formula $RR'R''E_{14}$— in which $E_{14}$ represents a carbon or silicon atom and R, R' and R" represent, independently, the hydrogen atom or an alkyl radical; $R_{15}$ represents in particular the isopropyl radical and $Me_3Si$, $L_3$ represents a group of formula —$E_{15}(R_{15})$— in which $E_{15}$ is a nitrogen or phosphorus atom and $R_{15}$ represents an alkyl radical, in particular methyl, or a radical of formula $RR'R''E_{14}$— in which $E_{14}$ represents a silicon atom and R, R' and R" represent, independently, an alkyl radical, and in particular methyl; and $R_1$ represents the hydrogen atom.

More particularly, a subject of the invention is the products described below in the examples, in particular products corresponding to the following formulae:
—[(Me$_3$SiNCH$_2$CH$_2$)$_2$NSiMe$_3$]AlCl;
—[(Me$_3$SiNCH$_2$CH$_2$)$_2$NMe]AlCl;
—[(Me$_3$SiNCH$_2$CH$_2$)$_2$NMe]AlH;
—[(Me$_3$SiNCH$_2$CH$_2$)$_2$NMe]AlCH$_3$;
—[(Me$_3$SiNCH$_2$CH$_2$)$_2$NSiMe$_3$]GaCl;
—{[((CH$_3$)$_2$CHNCH$_2$CH$_2$)((CH$_3$)$_2$CHNHCH$_2$CH$_2$)NMe]AlCl}{AlCl$_4$};
—{[(Me$_3$SiNCH$_2$CH$_2$)(Me$_3$SiNHCH$_2$CH$_2$)NSiMe$_3$]AlCl}{(AlCl$_4$)}.

A subject of the invention is also a process for the preparation of products of general formula 1 and 2 as defined above, characterized in that a product of formula I in which $L_1$, A, $L_3$, B and $L_2$ have the meanings indicated above and Y represents an organometallic group, a metal or the hydrogen atom, is reacted with a product of formula II in which $R_M$ and M have the meanings indicated above and $Z_1$ and $Z_2$ represent, independently, a parting group, in order to obtain a product of formula 1 which product of formula (1) can be reacted with a compound of formula (III)

in which $R_1$ and $X_1$ have the meaning indicated above, in order to obtain the corresponding product of formula 2.

The reaction of a compound of general formula I with a compound of general formula II in order to obtain a compound of general formula 1 can be carried out, under an inert atmosphere such as a freon or argon atmosphere, in an aprotic solvent, at a temperature comprised between −60 and +50° C. On carrying out the reaction which produced compound 2 starting from the corresponding compound 1, compound 1 is reacted, under an inert atmosphere and at ambient temperature, with a compound III in an aprotic medium.

A subject of the invention is also a process for the preparation of products of general formula 2 as defined above, characterized in that a product of formula (IV)

in which $R_1$, $L_1$, A, $L_3$, B and $L_2$ have the meanings indicated above and X represents a coordinating anion with respect to element M, is reacted with a compound of formula (V)

in which M has the meaning indicated above and X' represents the halogen atom, an alkyl or alkoxy radical as defined previously, in order to obtain the corresponding product 2.

The reaction which obtains a compound of general formula 2 from the corresponding compound of general formula IV can be carried out, under an inert atmosphere such as a freon or argon atmosphere, at ambient temperature with compound V in an aprotic medium. Compound 2 can also be obtained from compound IV according to another method known to a person skilled in the art, allowing removal of a coordinating anion of an element of group 13.

Whatever the preparation method implemented, the compounds 1 and 2 thus obtained are purified using standard purification methods. Compound 2 can also be prepared in situ, starting from compound IV, in the medium in which it is later used.

The product of formula IV can be obtained by reacting a compound of formula VI $$(R_1L_1\text{—}A\text{—}L_3\text{—}B\text{—}L_2)^-, Y_1^+ \qquad (VI)$$

in which $R_1$, $L_1$, A, $L_3$, B and $L_2$ have the meanings indicated above and $Y_1$ represents an organometallic group, a metal or the hydrogen atom, is reacted with a product of formula VII $$R_M MXZ_3 \qquad (VII)$$

in which $R_M$, M and X have the meanings indicated above and $Z_3$ represents a parting group. The reaction can be implemented under an inert atmosphere such as a freon or argon atmosphere, in an aprotic solvent, at a temperature comprised between −60 and +50° C.

The product of formula IV can also be obtained by reacting a compound of formula 1 as defined above with a compound of formula (VIII) $R_1X$ in which $R_1$ and X have the meaning indicated above. The reaction can be implemented under an inert atmosphere such as a freon or argon atmosphere, in an aprotic solvent, at a temperature comprised between −60 and +50° C.

As an aprotic solvent, there can be used the aromatic hydrocarbons such as benzene, toluene; aliphatic hydrocarbons such as pentane, heptane, hexane, cyclohexane; ethers such as diethyl ether, dioxane, tetrahydrofuran, ethyltertiobutyl ether.

In compounds I and VI, Y and $Y_1$ represent, independently, an organometallic group, a metal or the hydrogen atom. The organometallic group can be a compound of formula $R'''M_1$ or $R'''_3M_2$ in which $R'''$ represents an alkyl, cycloalkyl, aryl, alkoxy, cycloalkoxy or aryloxy radical defined as previously, $M_1$ is a zinc or mercury atom and $M_2$ a tin or lead atom, preferably, the organometallic group is chosen from the groups ZnMe, $SnMe_3$, $SnBu_3$ or $PbMe_3$. The metal can be an alkali metal chosen from lithium, sodium or potassium, or an alkaline earth metal such as magnesium.

In compounds II and VII, $Z_1$, $Z_2$ and $Z_3$ represent, independently a parting group such as a halogen atom, an alkyl, cycloalkyl, alkoxy, aryl or aryloxy group defined as above, or also a methanesulphonyloxy, a benzenesulphonyloxy, p-toluenesulphonyloxy.

In compound IV, X represents a coordinating anion with respect to element M. Anion X can be an anion of halogen or chalcogen type. Preferably, X represents a chlorine or bromine atom.

The starting product of formula I and the product of formula VI are known products or can be prepared from known products. For their synthesis, the following references can be mentioned: Cloke et al., J. Chem. Soc., Dalton Trans. (1995) 25. Wilkinson and Stone, Comprehensive Organometallic Chemistry (1982) vol. 1, 557.

The products of formula III and VIII are commercial or can be produced by methods known to a person skilled in the art.

The products of formula IV are new. Therefore, a subject of the invention is also, as new industrial products, the compounds of formula IV as defined above.

A subject of the invention is also the use of products of formula 1 and 2 as defined above, as catalysts for the implementation of (co)polymerization, i.e. of polymerization or copolymerization. The compounds of formula 1 and 2 are particularly useful for the implementation of the polymerization of heterocycles. The heterocycles can contain one or more heteroatoms of groups 15 and/or 16, and have a size ranging from three to eight members. As an example of heterocycles corresponding to the above formulation, there can be mentioned epoxides, thioepoxides, cyclic esters or thioesters such as lactones, lactames and anhydrides. The compounds of formula 1 and 2 are also particularly useful for the implementation of the (co)polymerization of cyclic esters. As an example of cyclic esters, there can be mentioned the polymer cyclic esters of lactic and/or glycolic acid. Random or block copolymers can be obtained according to whether the monomers are introduced together at the beginning of the reaction, or sequentially during the reaction.

A subject of the invention is also a process for the preparation of polymers or copolymers which consists in bringing into contact one or more monomers, a polymerization catalyst and a polymerization solvent, characterized in that the polymerization catalyst is chosen from the products of the invention.

The reaction solvent can be the (or one of the) substrate(s) used in the catalytic reaction. Solvents which do not interfere with the catalytic reaction itself are also suitable. As examples of such solvents, there can be mentioned saturated or aromatic hydrocarbons, ethers, aliphatic or aromatic halides.

The reactions are carried out at temperatures comprised between ambient temperature and approximately 150° C.; the temperature range comprised between 40 and 100° C. is most advantageous. Reaction durations are comprised between 1 and 300 hours, and preferably between 4 and 72 hours.

The products are generally recovered after adding, to the reaction medium, a protic solvent such as an alcohol, or an aprotic solvent such as tetrahydrofuran, followed by the removal of the compounds of element M by centrifugation.

This (co)polymerization process is particularly suitable for obtaining (co)polymers of cyclic esters, in particular the polymer cyclic esters of lactic and/or glycolic acid. The products obtained such as the glycolic lactic copolymer, which are biodegradable, are advantageously used as supports in sustained release therapeutic compositions. The process is also particularly suitable for the polymerization of epoxides, in particular of propene oxide. The polymers obtained are compounds which can be used for the synthesis of organic liquid crystals or also as semi-permeable membranes.

The following examples are presented in order to illustrate the above procedures and should in no event be considered to limit the scope of the invention.

EXAMPLE 1: $[(Me_3SiNCH_2CH_2)_2NSiMe_3]AlCl$

Figure 1:
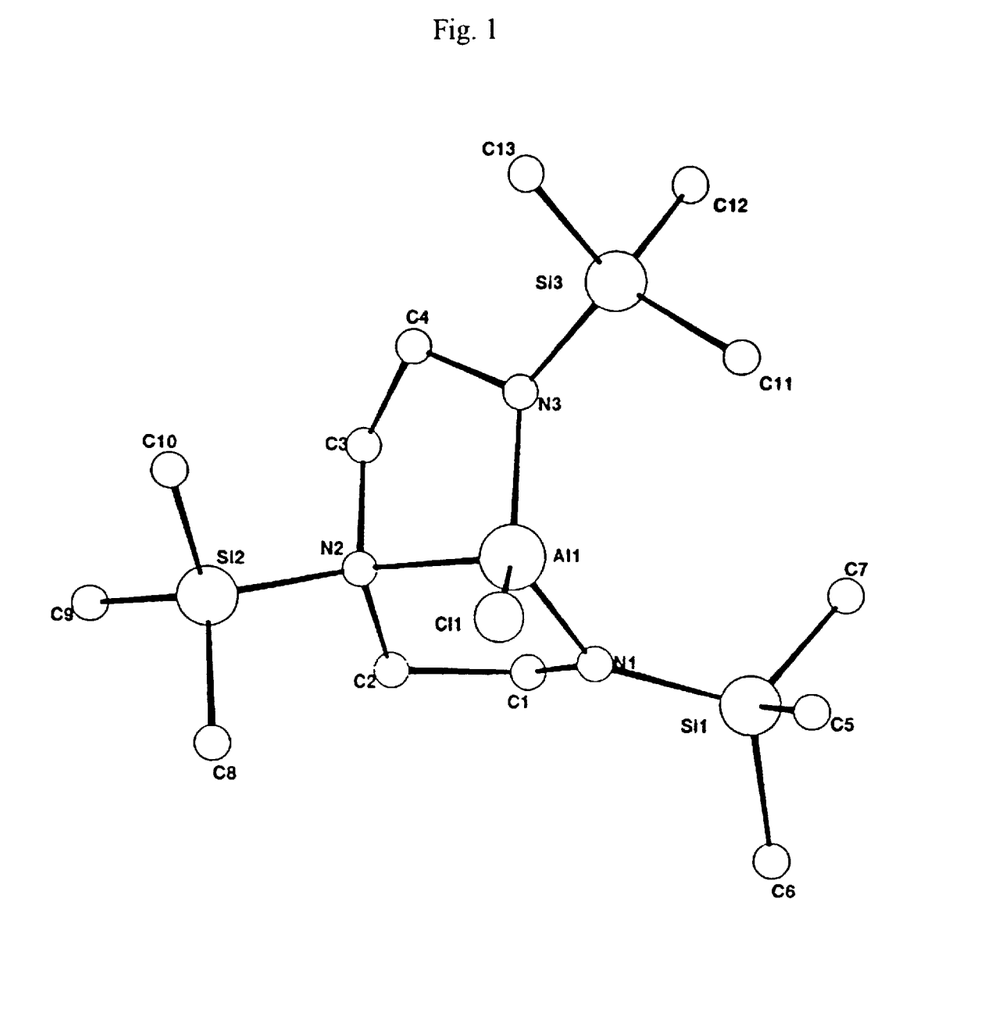

Compound 1 in which M=Al; $R_M$=Cl; A=B=—$CH_2CH_2$—;

$L_1$=$L_2$=$L_3$=$NSiMe_3$ 3.26 g (9.6 mmol) of $[(Me_3SiNCH_2CH_2)_2NSiMe_3]^{2-}$, $2Li^+$ and 100 ml of tetrahydrofuran are introduced successively into a Schlenk tube equipped with a magnetic stirrer and purged under argon. The reaction medium is cooled down to −40° C., then 1.33 g (10 mmol) of aluminium trichloride in solution in 100 ml of tetrahydrofuran is introduced. The reaction medium is allowed to return to ambient temperature then left under agitation at ambient temperature for 18 hours. The solvent is then evaporated off. The residue is sublimated under vacuum (0.05 torr) at 80° C. The desired compound is isolated in the form of white crystals. This compound is characterized by X-ray diffraction (FIG. 1 and Table 1 below). Melting point 10–13° C.

EXAMPLE 2: [(Me$_3$SiNCH$_2$CH$_2$)$_2$NMe]AlCl

Compound 1 in which M=Al; R$_M$=Cl; A=B=—CH$_2$CH$_2$—;

L$_1$=L$_2$=NSiMe$_3$; L$_3$=NMe

Figure 2:
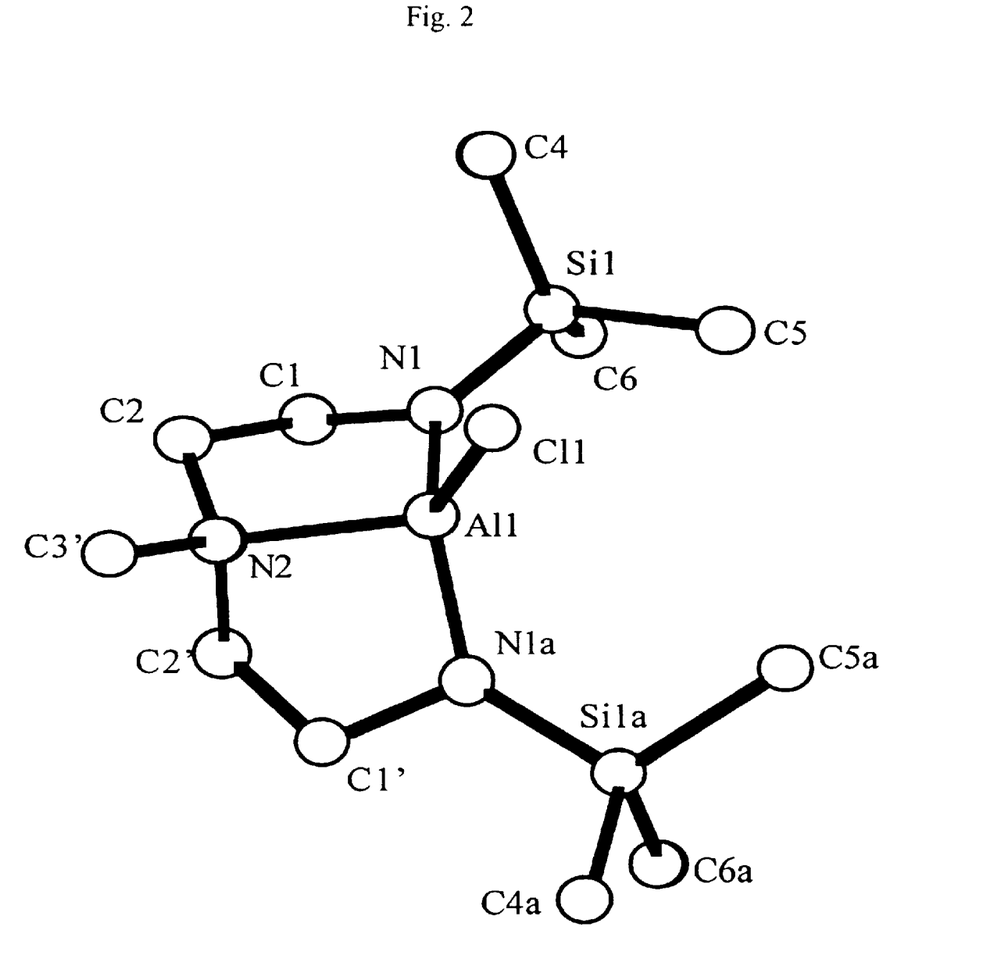

This compound is prepared according to the procedure described above. This compound is characterized by X-ray diffraction (FIG. 2 and Table 1 below). Melting point 130° C. (decomposition).

EXAMPLE 3: [(Me$_3$SiNCH$_2$CH$_2$)$_2$NMe]AlH

Compound 1 in which M=Al; R$_M$=H; A=B=—CH$_2$CH$_2$—

Figure 3:
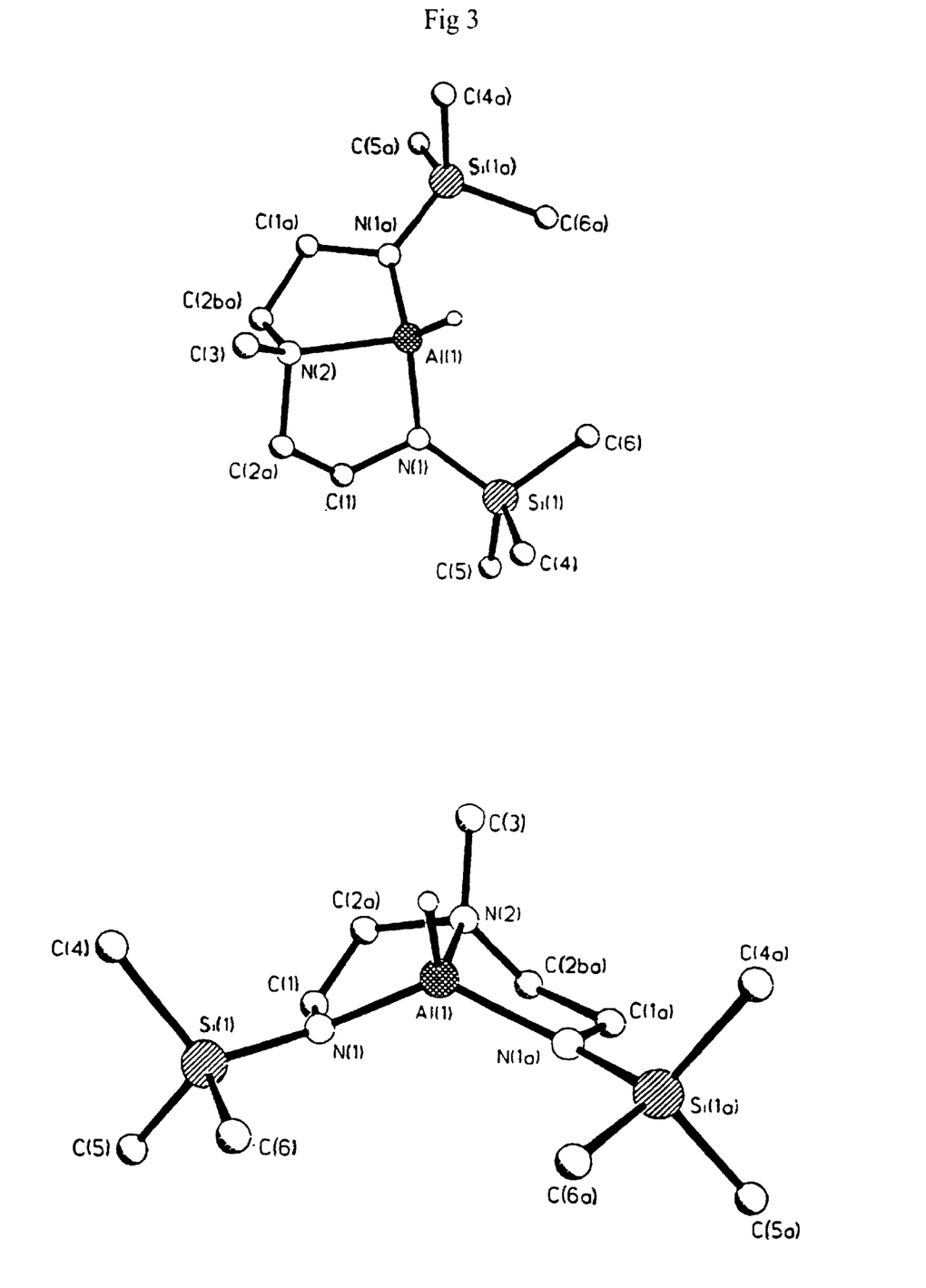

L$_1$=L$_2$=NSiMe$_3$; L$_3$=NMe 2.30 g (8.8 mmol) of (Me$_3$SiNHCH$_2$CH$_2$)$_2$NMe and 50 ml of tetrahydrofuran are introduced successively into a Schienk tube equipped with a magnetic stirrer and purged under argon. The reaction medium is cooled down to −40° C., then 0.33 g (8.8 mmol) of LiAlH$_4$ in suspension in 70 ml of tetrahydrofuran is introduced. Evolution of a gas is observed. The reaction medium is allowed to return to ambient temperature; it is left under agitation at ambient temperature for 18 hours. After filtering, the solvent is evaporated off then the residue is sublimated under vacuum (0.05 torr) at 90° C. The desired compound is isolated in the form of white crystals. This compound is characterized by X-ray diffraction (FIG. 3 and Table 1 below). Melting point 15° C.

EXAMPLE 4: [(Me$_3$SiNCH$_2$CH$_2$)$_2$NMe]AlCH$_3$

Compound 1 in which M=Al; R$_M$CH$_3$; A=B=—CH$_2$CH$_2$—

Figure 4:
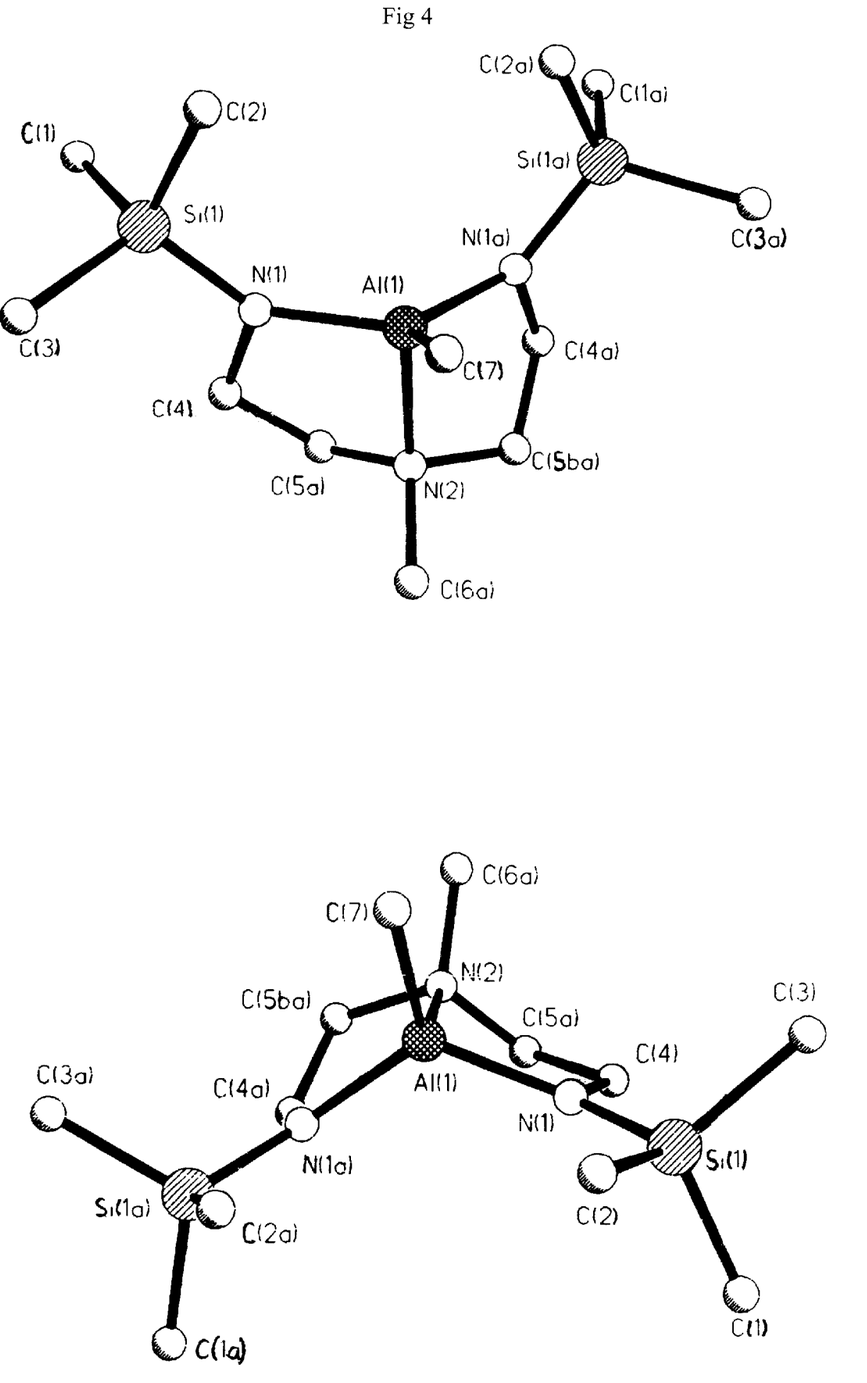

L$_1$=L$_2$=NSiMe$_3$; L$_3$=NMe 3.53 g (8.8 mmol) of (Me$_3$SiNHCH$_2$CH$_2$)$_2$NMe and 50 ml of tetrahydrofuran are introduced successively into a Schlenk tube equipped with a magnetic stirrer and purged under argon. The reaction mixture is cooled down to −60° C., then 6.7 ml of a 2M toluenic solution of AlMe$_3$ is introduced. The reaction mixture is allowed to return to ambient temperature, then heated at 100° C. for 12 hours. The solvent is evaporated off then the residue is sublimated under vacuum (0.05 torr) at 70° C. The desired compound is isolated in the form of white crystals. This compound is characterized by X-ray diffraction (FIG. 4 and Table 1 below). Melting point 67° C.

EXAMPLE 5: [(Me$_3$SiNCH$_2$CH$_2$)$_2$NSiMe$_3$]GaCl

Compound 1 in which M=Ga; R$_M$=Cl; A B=—CH$_2$CH$_2$—

L$_1$=L$_2$=L$_{3=NSiMe3}$ 1.34 g (4.0 mmol) of [(Me$_3$SiNCH$_2$CH$_2$)$_2$NSiMe$_3$]$^{2-}$, 2Li$^+$ and 50 ml of tetrahydrofuran are introduced successively into a Schlenk tube equipped with a magnetic stirrer and purged under argon. The reaction mixture is cooled down to −40° C., then 0.33 (8.8 mmol) of GaCl$_3$ in solution in 50 ml of tetrahydrofuran is introduced. The reaction mixture is allowed to return to ambient temperature, then left under agitation at ambient temperature for 18 hours. The formation of a precipitate is observed. After filtering, the solvent is evaporated off. The residue is sublimated under vacuum (0.05 torr) at 90° C. The desired compound is isolated in the form of white crystals. This compound is characterized by multinuclear magnetic resonance. Melting point 62° C.

NMR $^1$H(C$_6$D$_6$; 400 MHz): 0.18 (s, SiCH$_3$, 9H); 0.46 (s, SiCH$_3$, 18H); 1.98 (ddd, J=12.2; 5.0; 5.0 Hz; CH$_2$, 2H); 2.44 (ddd, J=12.2; 7.4; 5.2 Hz; CH$_2$, 2H), 2.94 (ddd, J=12.2; 5.0; 5.0 Hz; CH$_2$, 2H); 3.00 (ddd, J=12.2; 7.4; 5.0 Hz; CH$_2$, 2H).

NMR $^{13}$C{$^1$H}(C$_6$D$_6$; 100.63 MHz): 1.42 (SiCH$_3$), 1.82 (SiCH$_3$), 44.20 (CH$_2$); 54.21 (CH$_2$).

NMR $^{29}$Si(C$_6$D$_6$; 79.49 MHz): −3.70; −3.05.

EXAMPLE 6: {[((CH$_3$)$_2$CHNCH$_2$CH$_2$)((CH$_3$)$_2$CHNHCH$_2$CH$_2$)NMe]AlCl}{AlCl$_4$}

Compound 2 in which M=Al; R$_M$=Cl; R$_1$=H; A=B=—CH$_2$CH$_2$—

Figure 5:
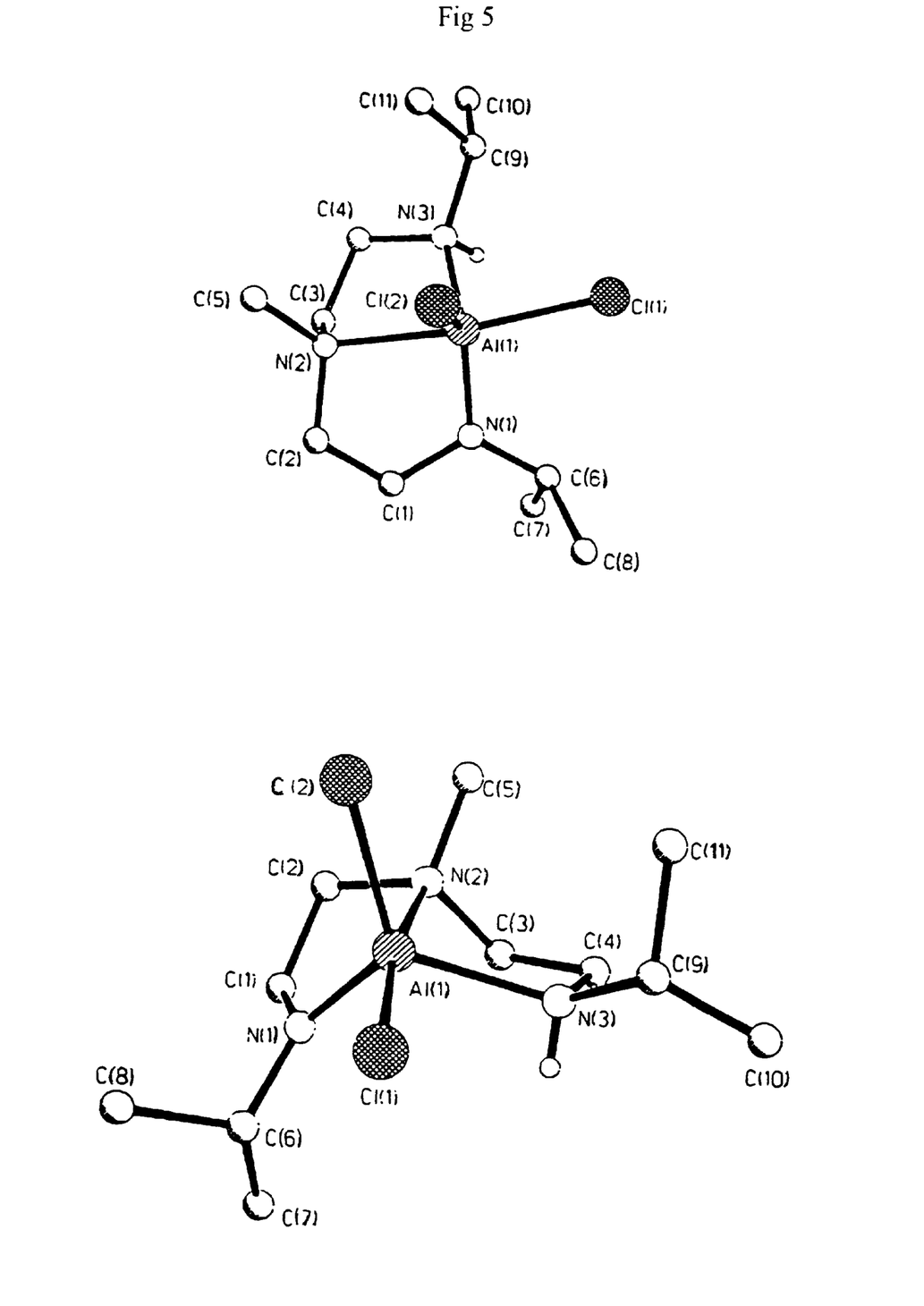

L$_1$=L$_2$=NCH(CH$_3$)$_2$; L$_3$=NMe; X$_1$$^-$=AlCl$_4$$^-$ 1.03 g (3.2 mmol) of [Me$_2$CHNCH$_2$CH$_2$)$_2$NCH$_3$]AlCl and 30 ml of toluene are introduced successively into a Schlenk tube equipped with a magnetic stirrer and purged under argon. The reaction mixture is cooled down to −40° C., then 3.2 mmol of hydrochloric acid in solution in diethyl ether is introduced. The reaction mixture is allowed to return to ambient temperature; it is left under agitation at ambient temperature for 18 hours. The solvent is then evaporated off to a volume of 5 ml and left at −30° C. The compound (IV) thus obtained is isolated in the form of white crystals. This compound is characterized by X-ray diffraction (FIG. 5 and Table 1 below; melting point 160° C. (decomposition)). Addition of one equivalent of aluminium trichloride in suspension in toluene allows the desired compound to be obtained.

EXAMPLE 7: {[(Me$_3$SiNCH$_2$CH$_2$)(Me$_3$SiNHCH$_2$CH$_2$)NSiMe$_3$]AlCl}{AlCl$_4$}

Compound 2 in which M=Al; R$_M$=Cl; R$_1$=H; A=B=—CH$_2$CH$_2$—

Figure 6:
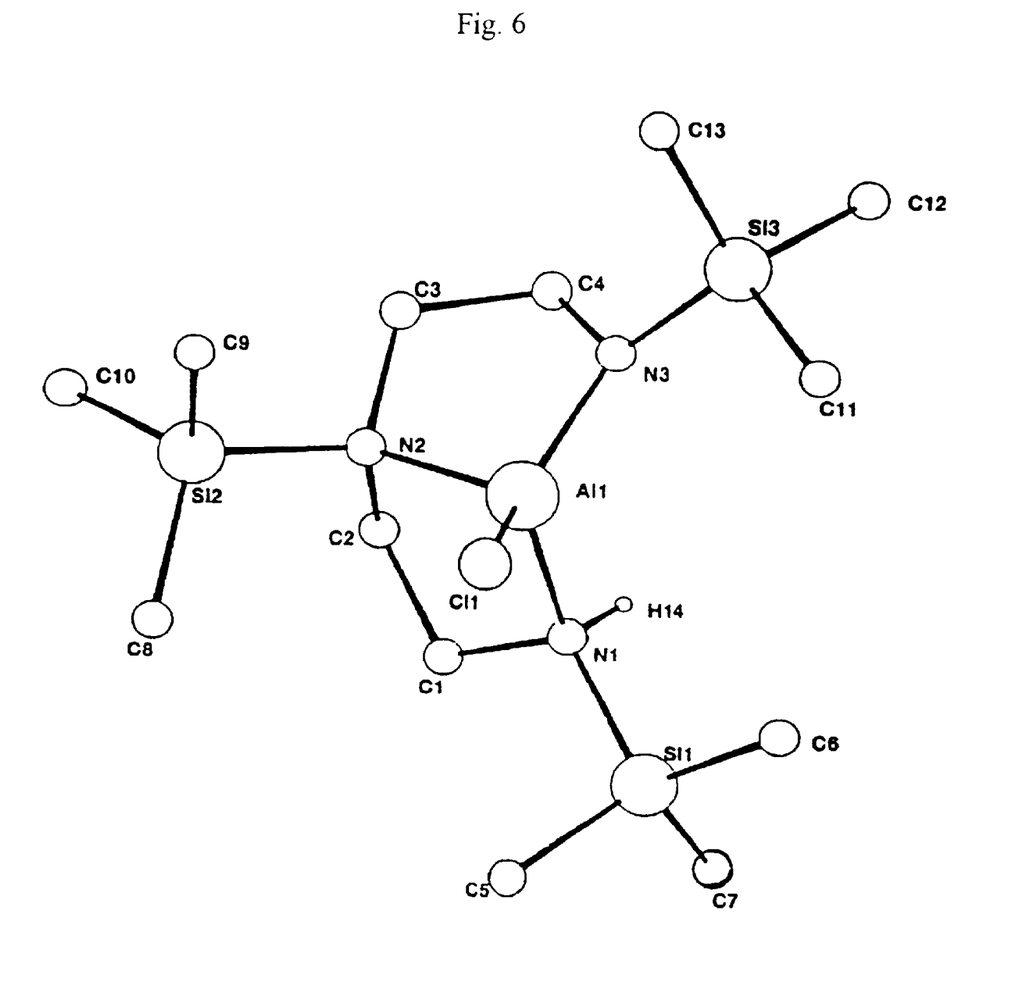

L$_1$=L$_2$=L$_3$=NSiMe$_3$; X$^-$=AlCl$^-$ 0.19 g (0.5 mmol) of [(Me$_3$SiNCH$_2$CH$_2$)$_2$NSiMe$_3$]AlCl, 4 ml of toluene and 1 mmol of hydrochloric acid in solution in diethyl ether are introduced successively into a Schlenk tube equipped with a magnetic stirrer and purged under argon. The formation of a precipitate is observed. 89 mg (0.67 mmol) of aluminium trichloride in suspension in 3 ml of toluene is then added at ambient temperature. The reaction mixture becomes homogenous again; it is left under agitation at ambient temperature for one hour. The solvent is then evaporated off to a volume of 0.5 ml and left at ambient temperature. The desired compound is isolated in the form of white crystals. This compound is characterized by X-ray diffraction (FIG. 6 and Table 1 below).

EXAMPLE 8: Polymerization of Propene Oxide 0.15 g (0.4 mmol) of [(Me$_3$SiNCH$_2$CH$_2$)$_2$NSiMe$_3$]AlCl and 4.5 ml (63 mmol) of propene oxide are introduced successively into a Schienk tube equipped with a magnetic stirrer and purged under argon. The reaction mixture is left under agitation at 30° C. for 144 hours, the excess propene oxide is evaporated off, then 20 ml of methanol is added. After centrifugation, the liquid phase is recovered, and the solvent evaporated off 0.55 g of a mixture or oligomers and polymers is obtained. This mixture is characterized by NMR of the carbon and the proton. According to GPC (Gel Permeation Chromatography) analysis using calibration carried out starting from polyethylene glycol (PEG) standards with masses of 194 to 22000 and extrapolated for higher masses, the sample is composed of oligomers of 798 dalton mean masses and polymers having similar masses (Mw/Mn=1.69) and Mw=106904 daltons.

EXAMPLE 9: Polymerization of Propene Oxide

The operating conditions art those of Example 8, except that the chiral cation $\{[(Me_3SiNCH_2CH_2)(Me_3SiNHCH_2CH_2)NSiMe_3]AlCl\}\{AlCl_4\}$ is used as a catalyst. After centrifugation, the liquid phase is recovered, and the solvent is evaporated off 2.17 g of a mixture of polymers is obtained. This polymer is characterized by NMR of the carbon and the proton. According to GPC analysis using calibration carried out from polyethylene glycol (PEG) standards of masses 194 to 22000, the sample is a mixture of polymers of very similar masses (Mw/Mn=1.17) and Mw=1446 daltons.

mmol) of propylene oxide are introduced successively into a Schlenk tube equipped with a magnetic stirrer and purged under argon. The reaction mixture is left under agitation at 30° C. for 1.5 hours, then the propylene oxide is evaporated off. 1.15 g of D,L-lactide, 0.93 g of glycolide and 30 ml ofibenzene are added successively. The reaction mixture is left under agitation at 80° C. for 240 hours. The solvent is evaporated off, then 20 ml of THF is added. After centrifugation, the liquid phase is recovered and the solvent evaporated off. 1.47 g of a mixture of copolymers is, obtained. This mixture is characterized by NMR of the carbon and proton. According to GPC analysis using calibration carried out from polyethylene glycol standards of masses 194 to 22000 and extrapolated for higher masses, the sample is a mixture of copolymers (Mw/Mn=1.98) and Mw=1962.

TABLE 1 length of selected bonds (in Angströms) and bond angles (in degrees) for the compounds of Examples 1 to 4 and 6 to 7.

| | Example 1 | Example 2 | Example 3 | Example 4 | Example 6 | Example 7 |
|---|---|---|---|---|---|---|
| Al(1)—Cl(1) | 2.144(1) Å | 2.148(3) Å | — | — | 2.2584(14) Å | 2.103(2) Å |
| Al(1)—Cl(2) | — | — | — | — | 2.2056(14) Å | — |
| Al(1)—C(7) | — | — | — | 1.963(3) Å | — | — |
| Al(1)—N(1) | 1.811(1) Å | 1.816(3) Å | 1.833(2) Å | 1.837(2) Å | 1.819(3) Å | 1.947(3) Å |
| Al(1)—N(2) | 1.998(1) Å | 1.991(3) Å | 2.016(3) Å | 2.018(2) Å | 2.103(3) Å | 1.963(3) Å |
| Al(1)—N(3) | 1.803(1) Å | — | — | — | 2.041(3) Å | 1.782(3) Å |
| Al(1)—N(1a) | — | 1.816(3) Å | 1.833(3) Å | 1.837(2) Å | — | — |
| N(1)—Al(1)—N(2) | 92.8(1)° | 91.1(1)° | 89.76(8)° | 89.77(7)° | 82.99(13)° | 91.8(1)° |
| N(1a)—Al(1)—N(2) | — | 91.9(1)° | 89.76(8)° | 89.77(7)° | — | — |
| N(1a)—Al(1)—N(1) | — | 126.3(1)° | 125.47(14)° | 122.35(12)° | — | — |
| N(1)—Al(1)—N(3) | 124.4(1)° | — | — | — | 115.28(14)° | 114.8(1)° |
| N(2)—Al(1)—N(3) | 92.8(1) | — | — | — | 81.98(12)° | 95.0(1)° |
| Cl(1)—Al(1)—N(1) | 113.1(1) | 113.7(1)° | — | — | 100.09(12)° | 109.4(1)° |
| Cl(1)—Al(1)—N(2) | 116.5(1)° | 112.7(1)° | — | — | 171.58(9)° | 117.9(1)° |
| Cl(1)—Al(1)—N(3) | 113.1(1)° | — | — | — | 89.63(10)° | 123.0(1)° |
| Cl(1)—Al(1)—N(1a) | — | 113.7(1)° | — | — | — | — |
| Cl(2)—Al(1)—N(1) | — | — | — | — | 121.84(11)° | — |
| Cl(2)—Al(1)—N(2) | — | — | — | — | 91.12(9)° | — |
| Cl(2)—Al(1)—N(3) | — | — | — | — | 121.03(10)° | — |
| C(7)—Al(1)—N(1) | — | — | — | 116.08(6)° | — | — |
| C(7)—Al(1)—N(1) | — | — | — | 116.08(6)° | — | — |
| C(7)—Al(1)—N(1) | — | — | — | 114.69(13)° | — | — |

EXAMPLE 10: Polymerization of D,L-lactide

0.05 g (0.17 mmol) of $[(Me_3SiNCH_2CH_2)_2NMe]AlH$, 1.15 g of D,L-lactide and 30 ml of toluene are introduced successively into a Schlenk tube equipped with a magnetic stirrer and purged under argon. The reaction mixture is left under agitation at 80° C. for 120 hours. The solvent is evaporated off, then 20 ml of THF is added. After centrifugation, the liquid phase is recovered and the solvent evaporated off 1.04 g of a mixture of D,Llactide (32%) and polymers (68%) is obtained. This mixture is characterized by NMR of thee carbon and the proton. According to GPC analysis using calibration carried out from polyethylene glycol standards of masses 194 to 22000 and extrapolated for higher masses, the polymers are a mixture of macromolecules of similar masses (Mw/Mn=1.61) and Mw=21659.

EXAMPLE 11: Polymerization of a D,L-lactide and Glycolide Mixture

0.08 g (0.17 mmol) of $\{[(Me_3SiNCH_2CH_2)(Me_3SiNHCH_2CH_2)NSiMe_3]AlCl\}\{AlCl_4\}$, 0.17 g (3

What is claimed is:

1. A compound selected from the group consisting of (1)

(2)

wherein M is an element of group 13, $R_M$ is selected from the group consisting of hydrogen, halogen, unsubstituted or substituted alkyl of 1 to 6 carbon atoms, cycloalkyl of 3 to 7 carbon atoms, aryl, alkoxy of 1 to 6 carbon atoms, cycloalkoxy of 3 to 7 carbon atoms, aryloxy, alkylthio of 1 to 6 carbon atoms, cycloalkylthio of 3 to 7 carbon atoms and arylthio with the substituent for the substituted groups being selected from the group consisting of halogen, —CN, —NO$_2$ and alkyl of 1 to 6 carbon atoms, A and B are independently selected from the group consisting of alkylene of 2 to 4 carbon atoms unsubstituted or substituted with at least one member selected from the group consisting of alkyl of 1 to 6 carbon atoms, cycloalkyl of 3 to 7 carbon atoms and aryl, all unsubstituted or substituted with at least one member of the group consisting of halogen, —CN, —NO$_2$ and alkyl of 1 to 6 carbon atoms, L$_1$, L$_2$ and L$_3$ are independently —E$_{15}$(R$_{15}$)— wherein E$_{15}$ is an element of group 15, R$_{15}$ is selected from the group consisting of a) hydrogen, b) unsubstituted or substituted alkyl of 1 to 6 carbon atoms, cycloalkyl of 3 to 7 carbon atoms and aryl, the substituents for the substituted groups being selected from the group consisting of halogen, —CN, —NO$_2$ and alkyl of 1 to 6 carbon atoms, c) RR'R''E$_{14}$— wherein E$_{14}$ is an element of group 14, R, R' and R'' are independently selected from the group consisting of hydrogen and unsubstituted or substituted alkyl of 1 to 6 carbon atoms, cycloalkyl of 3 to 7 carbon atoms, aryl, alkoxy of 1 to 6 carbon atoms, cycloalkoxy of 3 to 7 carbon atoms, aryloxy, alkylthio of 1 to 6 carbon atoms, cycloalkylthio of 3 to 7 carbon atoms and arylthio with the substituent for the substituted groups being selected from the group consisting of halogen, —NO$_2$, —CN and alkyl of 1 to 6 carbon atoms and d) —SO$_2$R'$_{15}$, R'$_{15}$ is selected from the group consisting of halogen, alkyl of 1 to 6 carbon atoms, haloalkyl of 1 to 6 carbon atoms and aryl optionally substituted with at least one member of the group consisting of halogen and alkyl and haloalkyl of 1 to 6 carbon atoms, X$^-$ is a non-coordinating anion with respect to M, and R$_1$ is selected from the group consisting of a) hydrogen, b) RR'R''E$_{14}$— and c) unsubstituted or substituted alkyl of 1 to 6 carbon atoms, cycloalkyl of 3 to 7 carbon atoms and aryl, the substituents being selected from the group consisting of halogen —NO$_2$, —CN and alkyl of 1 to 6 carbon atoms.

2. A compounds of claim 1 selected from the group consisting of:

—[(Me$_3$SiNCH$_2$CH$_2$)$_2$NSiMe$_3$]AlCl;
—[(Me$_3$SiNCH$_2$CH$_2$)$_2$NMe]AlCl;
—[(Me$_3$SiNCH$_2$CH$_2$)$_2$NMe]AlH;
—[(Me$_3$SiNCH$_2$CH$_2$)$_2$NMe]AlCH$_3$;
—[(Me$_3$SiNCH$_2$CH$_2$)$_2$NSiMe$_3$]GaCl;
—{[((CH$_3$)$_2$CHNCH$_2$CH$_2$)((CH$_3$)$_2$CHNHCH$_2$CH$_2$)NMe]AlCl}{AlCl$_4$}; and
—{[(Me$_3$SiNCH$_2$CH$_2$)(Me$_3$SiNHCH$_2$CH$_2$)NSiMe$_3$]AlCl}{(AlCl$_4$}.

3. Preparation process for products of general formula 1 and 2 as defined in claim 1, characterized in that a product of formula I (I)

in which L$_1$, A, L$_3$, B and L$_2$ have the meanings indicated in claim 1 and Y represents an organometallic group, a metal or the hydrogen atom, is reacted with a product of formula II

R$_M$MZ$_1$Z$_2$   (II)

in which R$_M$ and M have the meanings indicated in claim 1 and Z$_1$ and Z$_2$ represent, independently, a parting group, in order to obtain a product of formula I

(1)

which product of formula (1) can be reacted with a compound of formula (III)

R$_1$X$_1$   (III)

in which R$_1$ and X$_1$ have the meaning indicated in claim 1, in order to obtain the corresponding product of formula 2.

4. Process for the preparation of products of general formula 2 as defined in claim 1, characterized in that a product of formula IV (IV)

in which R$_1$, L$_1$, A, L$_3$, B and L$_2$ have the meanings indicated in claim 1 and X represents a co-ordinating anion with respect to element M, is reacted with a compound of formula (V)

MX'$_3$   (V)

in which M has the meaning indicated in claim 1 and X' represents a halogen atom, an alkyl or alkoxy radical, in order to obtain the corresponding product 2.

5. A compound of claim 1 wherein M is selected from the group consisting of boron, aluminum and gallium, R$_M$ is selected from the group consisting of hydrogen, halogen and methyl, A and B are alkylene of 2 to 4 carbon atoms, L$_1$ and L$_2$ are independently —E$_{15}$(R$_{15}$)—, E$_{15}$ is nitrogen or phosphorus, R$_{15}$ is RR'R''E$_{14}$—, E$_{14}$ is carbon or silicon, R, R', R'' are independently hydrogen or alkyl of 1 to 6 carbon atoms, L$_3$ is —E$_{15}$(R$_{15}$)— wherein E$_{15}$ is nitrogen or phosphorus and R$_{15}$ is alkyl of 1 to 6 carbon atoms or RR'R''E$_{14}$—, E$_{14}$ is silicon and R, R' and R'' are independently alkyl of 1 to 6 carbon atoms and R$_1$ is hydrogen.

6. A compound of claim 5 wherein R$_M$ is chlorine and A and B are ethylene.

7. A compound of claim 1 wherein R$_M$ is selected from the group consisting of hydrogen, chlorine and methyl, A and B are ethylene, L$_1$ and L$_2$ are independently isopropylamino or Me$_3$SiN— and L$_3$ is methylamino or Me$_3$SiN—.

8. In a process for the preparation of polymers or copolymers by reacting at least one monomer, a polymerization catalyst and a polymerization solvent at room temperature to 150° C. for 1 to 300 hours, the improvement comprising using a compound of claim 1 as the polymerization catalyst.

9. The process of claim 8 wherein the monomer is selected from the group consisting of epoxides and cyclic esters.

10. The process of claim 9 wherein the monomer is propylene oxide.

11. The process of claim 9 wherein the monomer is at least one compound selected from the group consisting of cyclic esters of lactic acid and glycolic acid.

12. In a method of copolymerizing heterocyclic compounds, the improvement comprising using a copolymerization catalyst of claim 1.

13. In a method of copolymerizing propylene oxide, the improvement comprising using as a copolymerization catalyst a compound of claim 1.

14. In a copolymerization of polymeric cyclic esters of lactic acid and/or glycolic acid, the improvement comprising using as the copolymerization catalyst a compounds of claim 1.

15. A compound having the formula

IV wherein $R_1$, $L_1$, A, X, $RM_1$, $L_2$, $L_3$ and B have the definitions of claim 1.

* * * * *